(12) United States Patent
Weingarten

(10) Patent No.: US 7,294,737 B2
(45) Date of Patent: Nov. 13, 2007

(54) PROCESS OF PREPARING ESTERS AND ETHERS OF PROBUCOL AND DERIVATIVES THEREOF

(75) Inventor: M. David Weingarten, Cumming, GA (US)

(73) Assignee: AtheroGenics, Inc., Alpharetta, GA (US)

( * ) Notice: Subject to any disclaimer, the term of this patent is extended or adjusted under 35 U.S.C. 154(b) by 230 days.

(21) Appl. No.: 11/111,194

(22) Filed: Apr. 20, 2005

(65) Prior Publication Data

US 2005/0267187 A1 Dec. 1, 2005

Related U.S. Application Data

(60) Provisional application No. 60/564,267, filed on Apr. 20, 2004.

(51) Int. Cl.
*C07C 9/00* (2006.01)
*C07C 321/10* (2006.01)
*A01N 37/10* (2006.01)

(52) U.S. Cl. .................. 560/142; 514/543; 562/431

(58) Field of Classification Search ............. 560/142; 562/431; 514/543, 212.07, 258, 393; 540/579; 544/282; 548/302.1
See application file for complete search history.

(56) References Cited

U.S. PATENT DOCUMENTS

| | | | |
|---|---|---|---|
| 3,179,701 A | 4/1965 | Rocklin | |
| 3,485,843 A | 12/1969 | Wang | |
| 3,576,883 A | 4/1971 | Neuworth | |
| 3,704,327 A | 11/1972 | Neuworth | |
| 3,897,500 A | 7/1975 | Neuworth | |
| 3,952,064 A | 4/1976 | Whalley | |
| 4,076,841 A | 2/1978 | Wagner et al. | |
| 4,734,527 A | 3/1988 | Krauss | |
| 4,752,616 A | 6/1988 | Hall et al. | |
| 4,755,524 A | 7/1988 | Mueller et al. | |
| 4,954,514 A | 9/1990 | Kita et al. | |
| 5,155,250 A | 10/1992 | Parker et al. | |
| 5,206,247 A | 4/1993 | Regnier et al. | |
| 5,262,439 A * | 11/1993 | Parthasarathy | 514/548 |
| 5,294,724 A | 3/1994 | Jendralla et al. | |
| 5,608,095 A | 3/1997 | Parket et al. | |
| 5,627,205 A | 5/1997 | Regnier et al. | |
| 6,147,250 A * | 11/2000 | Somers | 560/130 |
| 6,323,359 B1 * | 11/2001 | Jass | 560/142 |
| 6,548,699 B1 | 4/2003 | Somers | |
| 6,602,914 B2 | 8/2003 | Meng | |
| 6,617,352 B2 | 9/2003 | Somers | |
| 6,747,061 B2 | 6/2004 | Medford et al. | |
| 6,828,447 B2 | 12/2004 | Meng | |
| 6,852,878 B2 | 2/2005 | Meng et al. | |
| 6,881,860 B2 | 4/2005 | Luchoomun et al. | |
| 6,960,683 B2 | 11/2005 | Meng | |
| 2002/0193446 A1 | 12/2002 | Meng | |
| 2004/0138147 A1 | 7/2004 | Glass et al. | |
| 2004/0204485 A1 | 10/2004 | Weingarten et al. | |
| 2004/0266879 A1 | 12/2004 | Sikorski et al. | |
| 2005/0090487 A1 | 4/2005 | Somers | |
| 2006/0079713 A1 | 4/2006 | Meng | |

FOREIGN PATENT DOCUMENTS

| | | |
|---|---|---|
| DE | 2716125 A1 | 10/1977 |
| EP | 0190682 A2 | 8/1986 |
| EP | 0317165 A1 | 5/1989 |
| EP | 0348203 A1 | 12/1989 |
| EP | 0405788 A2 | 1/1991 |
| EP | 0418648 A1 | 3/1991 |
| EP | 0621255 A1 | 10/1994 |
| EP | 0763527 A1 | 3/1997 |
| FR | 2130975 A5 | 11/1972 |
| FR | 2133024 A5 | 11/1972 |
| FR | 2134810 A5 | 12/1972 |
| FR | 2140769 A5 | 1/1973 |
| FR | 2140771 A5 | 1/1973 |
| FR | 2168137 A5 | 8/1973 |
| GB | 1136539 A | 12/1968 |
| GB | 1148550 A | 4/1969 |
| GB | 1199871 A | 7/1970 |
| GB | 1557622 A | 12/1979 |
| WO | WO96/12703 A1 | 5/1996 |

(Continued)

OTHER PUBLICATIONS

De Meglio, P., et al. ["New derivatives of clofibrate and probucol. Preliminary studies on hypolipemic activity,"] *Farmaco, Ed. Sci.*, 1985, 40(11), 833-844. (In Italian).
JP 06-312978 [94-312978] A, Nippon Tobacco Sangyo et al. [Kobayashi et al.], (Nov. 8, 1994).
JP 09-059258 [97-059258] A, Ono Pharm. Co. [Matsuo et al.], (Mar. 4, 1997).
JP 49-075552 [74-75,552] A2, Sagami Chemical Research Center [Fujisawa et al.], Jul. 20, 1974.
Kelarev, V.I., et al., ["Synthesis of mono- and disubstituted $\Delta^2$-imidazolines containing fragments of a sterically hindered phenol,"] *Khim. Geterotsikl. Soedin*, 1995(4):514-517 (1995) (In Russian).
Kelarev, V.I., et al., ["Synthesis and properties of s-triazine derivatives. 17. Synthesis of 2-methyl-4,6-disubstituted and 2,4-dimethyl-6-substituted s-triazines by reduction of trichloromethyl derivatives,"] *Khim. Geterotsikl. Soedin*, 1995(5): 667-673 (1995) (In Russian).

(Continued)

*Primary Examiner*—Kamal Saeed
*Assistant Examiner*—Janet L. Coppins
(74) *Attorney, Agent, or Firm*—King & Spalding

(57) ABSTRACT

Provided are methods for manufacturing compounds of Formula I

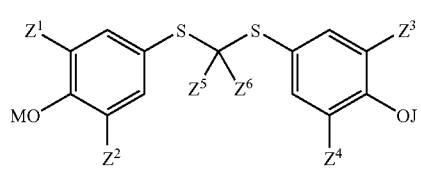

wherein all substituents are described herein.

11 Claims, No Drawings

FOREIGN PATENT DOCUMENTS

| | | |
|---|---|---|
| WO | WO97/15546 A1 | 5/1997 |
| WO | WO98/22418 A1 | 5/1998 |
| WO | WO98/51662 A2 | 11/1998 |
| WO | WO99/24400 A1 | 5/1999 |
| WO | WO 00/26184 A1 | 5/2000 |
| WO | WO 00/28332 A1 | 5/2000 |
| WO | WO 01/70757 A2 | 9/2001 |
| WO | WO 03/080568 A2 | 10/2003 |
| WO | WO 2004/062622 A2 | 7/2004 |

OTHER PUBLICATIONS

Mamedov, Ch.I., ["Synthesis of sulfur-containing derivatives of 2,6-di-tert-butylphenols,"] *Mater. Nauchn. Konf. Aspir. Akad. Nauk. Az. SSR*, 1:127-131 (1980), in Russian.

Medvedev, A.I., et al ., ["Synthesis and properties of some new derivatives, of 3,5-di-tert-butyl-4-hydroxythiophenol,"] *Tezisy Dokl. Nauchn. Sess. Khim. Teknol. Org. Soedin. Sery Sernistykh Neftei, 13$^{th}$*, Gal'pern, G.D., Ed. ("Zinatne", Riga, USSR, 1974), pp. 123-124 (In Russian).

Meng, C.Q., et al., "Novel phenolic antioxidants as multifunctional inhibitors of inducible VCAM-1 expression for use in atherosclerosis," *Bioorg. Med. Chem. Lett.*, 12:2545-2548 (2002).

Neuworth, M.B., et al. "Synthesis and hyopcholesterolemic activity of alkylidenedithio bisphenols," *J. Med. Chem.*, 13(4):722-725 (1970).

Sundell, et al., "AGIX-4207: A novel antioxidant and anti-inflammatory compound inhibits progression of collagen II arthritis in the rat," Annual Meeting of the Professional Research Scientists on Experimental Biology (Apr. 20-24, 2002), *FASEB Journal*, 16(4):A182, Abstract No. 168.4 (2002).

\* cited by examiner

PROCESS OF PREPARING ESTERS AND ETHERS OF PROBUCOL AND DERIVATIVES THEREOF

CROSS REFERENCE TO RELATED APPLICATIONS

This application claims priority to U.S. provisional patent application Ser. No. 60/564,267, filed Apr. 20, 2004.

FIELD OF THE INVENTION

The invention provides processes for the preparation of derivatives of probucol and, more specifically, to the preparation of ester and ether derivatives of probucol and derivatives thereof.

DESCRIPTION OF RELATED ART

The present invention provides a process for preparing substituted compounds which are useful as medicinal agents, particularly as atherogenic agents and as agents useful in the areas of post-percutaneous coronary intervention restenosis, atherosclerosis, and other cardiovascular or inflammatory diseases and disorders.

Several series of phenolic structural derivatives related to the probucol have been prepared and disclosed in the literature. U.S. Pat. No. 5,262,439 to Parthasarathy (issued Nov. 16, 1993), discloses analogs of probucol with increased water solubility in which one or both of the hydroxyl groups are replaced with ester groups that increase the water solubility of the compound. The '439 patent reports that carboxylic acid derivatives of probucol compounds (as that term is defined in the '439 patent) can be prepared by treating probucol compounds with an excess of dicarboxylic acid anhydride and catalytic amounts of 4-dimethylamino pyridine at a temperature sufficient to ensure that the dicarboxylic acid anhydride is liquid. According to the disclosure, no anhydrous solvent is necessary under these conditions, as the anhydride itself acts as a solvent.

In U.S. Pat. No. 6,147,250 (issued Nov. 14, 2000), compounds, compositions, methods for inhibiting the expression of VCAM-1, and methods of preparing such compounds and compositions are disclosed. The patent reports that monoesters of probucol can be prepared by treating probucol in tetrahydrofuran with sodium hydride and an acid chloride or acid anhydride. In one example using this process, a monoester of probucol is prepared in approximately 14% yield following purification by chromatographic methods.

U.S. Pat. No. 6,323,359 discloses and claims methods of manufacturing a group of probucol derivative compounds found in the '250 patent. The '359 patent discloses the use of alkali metal hydroxide, alkali metal alkoxide, alkali ammonium alkoxide, and alkyl ammonium hydroxide to form alkali metal salts of the probucol derivative compounds and then reacting the salts with a dicarboxylic acid anhydride.

A series of French patents have disclosed that certain probucol derivatives are hypocholesterolemic and hypolipemic agents: Fr 2.168.137 (bis-4-hydroxyphenylthioalkane esters); Fr 2140771 (tetralinyl phenoxy alkanoic esters of probucol); Fr 2.140.769 (benzofuryloxyalkanoic acid derivatives of probucol); Fr 2.134.810 (bis-(3-alkyl-5-alkyl-4-thiazole-5-carboxy)phenylthio)alkanes); Fr 2.133.024 (bis-(4-nicotinoyloxyphenylthio)propanes); and Fr 2.130.975 ((bis-(4-phenoxyalkanoyloxy)-phenylthio)alkanes). Most notable with regards to the production of probucol derivatives is French Patent Publication No. 2.168.137, which describes the production of diesters of probucol by reacting probucol with a halide or anhydride of an organic acid in an inert solvent with heat and in the presence of a base such as an alkaline hydroxide or carbonate, or a tertiary amine (e.g., triethylamine). The O-metal salt derivative of probucol is also suggested to be useful as the reaction intermediate.

U.S. patent application Ser. No. 10/757,664, filed Jan. 13, 2003, teaches processes for the preparation of esters and ethers of probucol by reacting probucol or a free hydroxyl-containing probucol derivative with a Grignard reagent or a lithium reagent to form a magnesium or lithium salt, followed by a reaction with an ester-forming or ether-forming compound.

It is thus an object of the present invention to provide a simple and efficient process for the preparation of a select group of compounds such as those described in U.S. Pat. Nos. 6,147,250; 6,323,359; and 5,262,439.

SUMMARY OF THE INVENTION

A facile process for the preparation of esters and ethers of probucol or probucol derivatives is provided.

The invention includes a process for the manufacturing of a compound of Formula I or its ester or salt thereof,

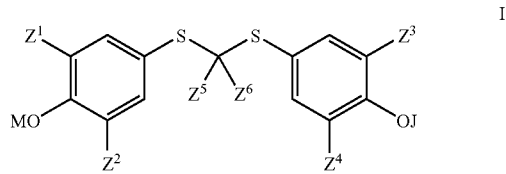

wherein $Z^1$, $Z^2$, $Z^3$, and $Z^4$ are independently selected from the group consisting of hydrogen and alkyl, said alkyl optionally substituted by hydroxy, alkyl, alkenyl, acyl, nitro, amino, halo, carboxy and cyano;

$Z^5$ and $Z^6$ are the same or different and independently selected from the group consisting of alkyl, alkenyl, and aryl all of which can be optionally substituted by hydroxy, alkyl, alkenyl, acyl, nitro, amino, halo, carboxy and cyano;

$Z^5$ and $Z^6$ can come together to form a carbocyclic ring;

M is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

or M is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality;

J is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

or J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;
the process comprising:
reacting a compound of Formula II,

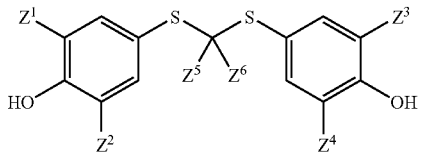

wherein $Z^1$, $Z^2$, $Z^3$, $Z^4$, $Z^5$ and $Z^6$ are as previously defined, with a compound of Formula III,

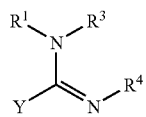

wherein Y is $R^2$ or $NR^2R^5$;
$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;
$R^1$ and $R^2$ can optionally come together to form a ring;
$R^3$ and $R^4$ can optionally come together to form a ring;

and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; or, a compound selected the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more substituents selected from the group consisting of protected hydroxy, alkyl, alkenyl, acyl, nitro, protected amino, halo, protected carboxy, epoxide and cyano; and, separating and isolating the compound of Formula I.

DEFINITIONS

The following definitions are provided in order to aid those skilled in the art in understanding the detailed description of the present invention.

The terms "alkyl" or "alk", alone or in combination, unless otherwise specified, means a saturated straight or branched primary, secondary, or tertiary hydrocarbon from 1 to 16 carbon atoms, including, but not limited to methyl, ethyl, propyl, isopropyl, butyl, isobutyl, t-butyl, and sec-butyl. The alkyl group may be optionally substituted where possible with any moiety that does not otherwise interfere with the reaction or that provides an improvement in the process, including but not limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art.

Whenever a range of is referred to herein, it includes independently and separately every member of the range. As a nonlimiting example, the term "$C_1$-$C_{10}$ alkyl" (or $C_{1-10}$ alkyl) is considered to include, independently, each member of the group, such that, for example, $C_1$-$C_{10}$ alkyl includes straight, branched and where appropriate cyclic $C_1$, $C_2$, $C_3$, $C_4$, $C_5$, $C_6$, $C_7$, $C_8$, $C_9$ and $C_{10}$ alkyl functionalities.

In the text, whenever the term "C(alkyl range)" is used, the term independently includes each member of that class as if specifically and separately set out. As a non-limiting example, the term "$C_{1-10}$" independently represents each species that falls within the scope, including, but not limited to, methyl, ethyl, propyl, isopropyl, butyl, sec-butyl, isobutyl, tert-butyl, pentyl, iso-pentyl, neo-pentyl, cyclopentyl, cyclopentyl, hexyl, 1-methylpentyl, 2-methylpentyl, 3-methylpentyl, 4-methylpentyl, 1-ethylbutyl, 2-ethylbutyl, 3-ethylbutyl, 4-ethyl butyl, cyclohexyl, heptyl, 1-methylhexyl, 2-methylhexyl, 3-methylhexyl, 4-methylhexyl, 5-methylhexyl, 6-methylhexyl, 1-ethylpentyl, 2-ethylpentyl, 3-ethylpentyl, 4-ethylpentyl, 5-ethylpenyl, 1-propylbutyl, 2-propylbutyl, 3-propybutyl, 4-propylbutyl, cycloheptyl, octyl, 1-methylheptyl, 2-methylheptyl, 3-methylheptyl, 4-methylheptyl, 5-methylheptyl, 6-methylheptyl, 7-methylheptyl, 1-ethylhexyl, 2-ethylhexyl, 3-ethylhexyl, 4-ethylhexyl, 5-ethylhexyl, 6-ethylhextyl, 1-propylpentyl, 2-propylpentyl, 3-propypentyl, 4-propylpentyl, 5-propylpentyl, cyclooctyl, nonyl, cyclononyl, decyl, or cyclodecyl.

The term "alkenyl", alone or in combination, means a non-cyclic alkyl of 2 to 10 carbon atoms having one or more unsaturated carbon-carbon bonds. The alkenyl group may be optionally substituted where possible with any moiety that does not otherwise interfere with the reaction or that provides an improvement in the process, including but not limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art.

The term "alkynyl", alone or in combination, means a non-cyclic alkyl of 2 to 10 carbon atoms having one or more triple carbon-carbon bonds, including but not limited to ethynyl and propynyl. The alkynyl group may be optionally substituted where possible with any moiety that does not otherwise interfere with the reaction or that provides an improvement in the process, including but not limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art.

The term "aryl", alone or in combination, means a carbocyclic aromatic system containing one, two or three rings wherein such rings may be attached together in a pendent manner or may be fused. The "aryl" group can be optionally substituted where possible with one or more of the moieties selected from the group consisting of alkyl, alkenyl, alkynyl, heteroaryl, heterocyclic, carbocycle, alkoxy, oxo, aryloxy, arylalkoxy, cycloalkyl, tetrazolyl, heteroaryloxy; heteroarylalkoxy, carbohydrate, amino acid, amino acid esters, amino acid amides, alditol, halogen, haloalkylthi, haloalkoxy, haloalkyl, hydroxyl, carboxyl, acyl, acyloxy, amino, aminoalkyl, aminoacyl, amido, alkylamino, dialkylamino, arylamino, nitro, cyano, thiol, imide, sulfonic acid, sulfate, sulfonate, sulfonyl, alkylsulfonyl, aminosulfonyl, alkylsulfonylamino, haloalkylsulfonyl, sulfanyl, sulfinyl, sulfamoyl, carboxylic ester, carboxylic acid, amide, phosphonyl, phosphinyl, phosphoryl, thioester, thioether, oxime, hydrazine, carbamate, phosphonic acid, phosphate, phosphonate, phosphinate, sulfonamido, carboxamido, hydroxamic acid, sulfonylimide or any other desired functional group that does not inhibit the pharmacological activity of this compound, either unprotected, or protected as necessary, as known to those skilled in the art. In addition, adjacent groups on an "aryl" ring may combine to form a 5- to 7-membered saturated or partially unsaturated carbocyclic, aryl, heteroaryl or heterocyclic ring, which in turn may be substituted as above.

The term "acyl", alone or in combination, means a group of the formula —C(O)R', wherein R' is alkyl, alkenyl, alkynyl, aryl, or aralkyl group.

The terms "carboxy", "COOH" and "C(O)OH" are used interchangeably.

The terms "halo" and "halogen" and "halide", alone or in combination, means chloro, bromo, iodo and fluoro.

The term "amino", alone or in combination, means a group of the formula NR'R", wherein R' and R" are independently selected from a group consisting of a bond, hydrogen, alkyl, aryl, alkaryl, and aralkyl, wherein said alkyl, aryl, alkaryl and aralkyl may be optionally substituted where possible as defined above.

The term "nitro", alone or in combination, denotes the radical —NO$_2$.

The term "substituted", means that one or more hydrogen on the designated atom or substituent is replaced with a selection from the indicated group, provided that the designated atom's normal valency is not exceeded, and the that the substitution results in a stable compound. When a substitutent is "oxo" (keto) (i.e., =O), then 2 hydrogens on the atom are replaced. If the term is used without an indicating group, an appropriate substituent known by those skilled in art may be substuteituted, including, but not limited to, hydroxyl, alkyl, alkenyl, acyl, nitro, protected amino, halo, protected carboxy, epoxide, and cyano.

The term "polar or charged functionality" means a polar or charged group attached in place of one or more hydrogen atoms. Non limiting examples include carboxy, hydroxy, amino, epoxide, etc.

The terms "protecting group" or "protected" means a substituent that protects various sensitive or reactive groups present, so as to prevent said groups from interfering with a reaction. Such protection may be carried out in a well-known manner as taught by Greene, T. M. and Wuts, P. G. M., in *Protective Groups in Organic Synthesis*, John Wiley and Sons, Third Edition, 1999; Kocienski, P. J., in *Protecting Groups*, Thieme Medical Publications, 2$^{nd}$ Edition, 2000; or similar texts. The protecting group may be removed after the reaction in any manner known by those skilled in the art.

Non-limiting examples of protecting groups include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenesulfonyl. For example, a protected carboxy could be selected from one of the following:

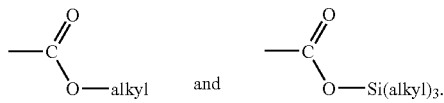

The terms "acid anhydride" and "carboxylic acid anhydride", alone or in combination means compounds having the formulas acyl-OC(O)R$^\alpha$, acyl-OC(O)OR$^\alpha$, acyl-OC(O)SR$^\alpha$, or acyl-OC(O)NR$^\alpha$R$^\beta$ wherein R$^\alpha$ is selected from the group consisting of alkyl, alkenyl, alkynyl, aryl, and aralkyl and R$^\beta$ is selected from the group consisting of alkyl, alkenyl, alkynyl, aryl, alkaryl, aralkyl and a protecting group (as that term is defined herein). The terms also include compounds having the formula

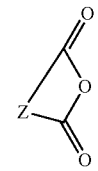

wherein Z is selected from alkyl, alkenyl, alkynyl, aryl, aralkyl and —(CH$_2$)NR$^\beta$. All "carboxylic acid anhydrides" and "acid anhydrides" may optionally be substituted as defined herein.

The term "activated carboxylic acid ester" means compounds having the formula C(O)SR" and C(O)OR", wherein R" is a substituted or unsubstituted aryl or an unsubstituted or substituted alkyl.

The term "epoxide" means the radical

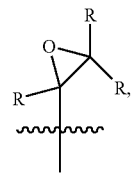

wherein all R groups are independently selected from hydrogen, alkyl, aryl and arylalkyl wherein said alkyl, aryl and arylalkyl may optionally be substituted with a polar functionality.

The terms "1,8-Diazabicyclo[5.4.0]undec-7-ene", "DBU" and the structure

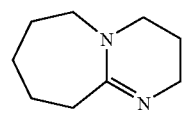

are used interchangeably.

The terms "1,5-Diazabicyclo[4.3.0]non-5-ene", "DBN" and the structure

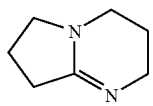

are used interchangeably.

The terms "esters of probucol" and "esters of probucol derivatives" are defined as probucol or probucol derivatives (as the case may be) wherein one or both of the phenol moieties are acylated. The term "monoesters of probucol" is defined as probucol wherein one of the phenol moieties are acylated. The term "diesters of probucol" is defined as probucol wherein both of the phenol moieties are acylated.

The terms "ethers of probucol" and "ethers of probucol derivatives" are defined as probucol or probucol derivatives (as the case may be) wherein one or both of the phenol moieties are alkylated.

The term "probucol derivative" refers to the compound

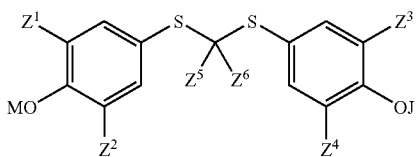

I wherein at least one $Z^1$, $Z^2$, $Z^3$, and $Z^4$ is other than t-butyl and/or one or both of $Z^5$ and $Z^6$ are other than methyl and/or one or both of M and J are other than hydrogen.

The terms "probucol monosuccinate", "MSP", and the sturucture

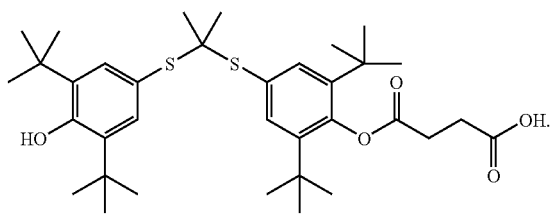

are used interchangeably.

The terms "probucol disuccinate", "DSP", and the structure

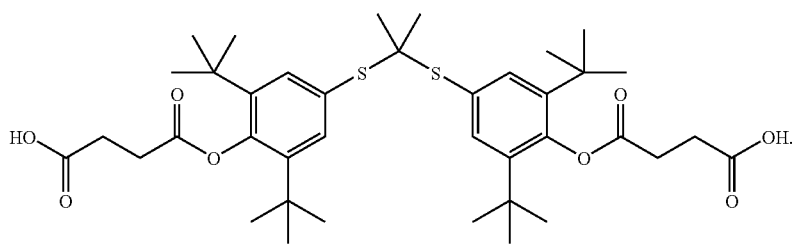

are used interchangeably.

DETAILED DESCRIPTION OF THE INVENTION

The present invention is concerned with processes for preparing compounds of Formula I, which are useful as medicinal agents, particularly (but not limited to) in the areas of post-percutaneous coronary intervention restenosis, atherosclerosis and other inflammatory diseases or disorders.

In a broad description, the invention encompasses the method of manufacturing a compound of Formula I or its ester or salt thereof,

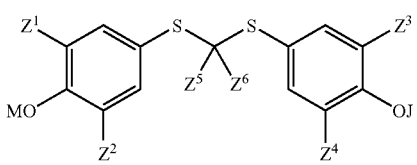

I wherein $Z^1$, $Z^2$, $Z^3$, and $Z^4$ are independently selected from the group consisting of hydrogen and alkyl, said alkyl optionally substituted by hydroxy, alkyl, alkenyl, acyl, nitro, amino, halo, carboxy and cyano;

$Z^5$ and $Z^6$ are the same or different and independently selected from the group consisting of alkyl, alkenyl, and aryl all of which can be optionally substituted by hydroxy, alkyl, alkenyl, acyl, nitro, amino, halo, carboxy and cyano;

$Z^5$ and $Z^6$ can come together to form a carbocyclic ring;

M is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

or M is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality;

J is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

or J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; the process comprising:

reacting a compound of Formula II,

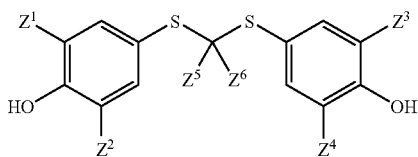

wherein $Z^1$, $Z^2$, $Z^3$, $Z^4$, $Z^5$ and $Z^6$ are as previously defined, with a compound of Formula III,

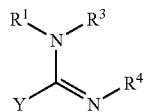

wherein Y is $R^2$ or $NR^2R^5$;

$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;

$R^1$ and $R^2$ can optionally come together to form a ring;

$R^3$ and $R^4$ can optionally come together to form a ring;

and a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano; or a compound selected the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano; and separating and isolating said compound of Formula I.

In a $2^{nd}$ embodiment, the invention is represented by the process to manufacture a compound of Formula I or its ester or salt thereof,

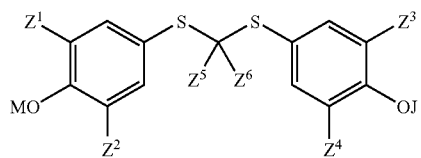

wherein $Z^1$, $Z^2$, $Z^3$, and $Z^4$ are independently selected from the group consisting of hydrogen and alkyl, said alkyl optionally substituted by hydroxy, alkyl, alkenyl, acyl, nitro, amino, halo, carboxy and cyano;

$Z^5$ and $Z^6$ are the same or different and independently selected from the group consisting of alkyl, alkenyl, and aryl all of which can be optionally substituted by hydroxy, alkyl, alkenyl, acyl, nitro, amino, halo, carboxy and cyano;

$Z^5$ and $Z^6$ can come together to form a carbocyclic ring;

M is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; and J is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

the process comprising:

reacting a compound of Formula II,

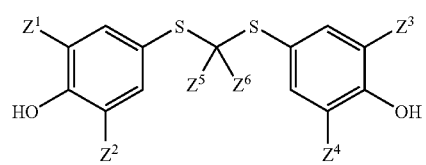

wherein $Z^1$, $Z^2$, $Z^3$, $Z^4$, $Z^5$ and $Z^6$ are as previously defined, with a compound of Formula III,

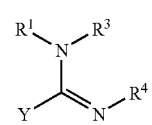

wherein Y is $R^2$ or $NR^2R^5$;

$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;

$R^1$ and $R^2$ can optionally come together to form a ring;

$R^3$ and $R^4$ can optionally come together to form a ring;

and a compound selected the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more selected from the group consisting of protected hydroxy, alkyl, alkenyl, acyl, nitro, protected amino, halo, protected carboxy, epoxide and cyano; and separating and isolating said compound of Formula I.

In a $3^{rd}$ embodiment, the invention is represented by the process to manufacture a compound of Formula IV or its ester or salt thereof,

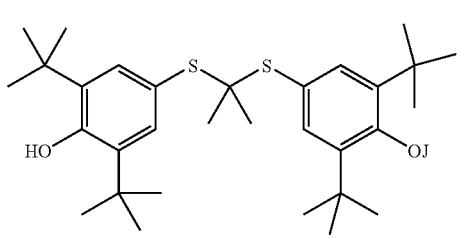

IV wherein J is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

the process comprising:

reacting a compound of Formula V,

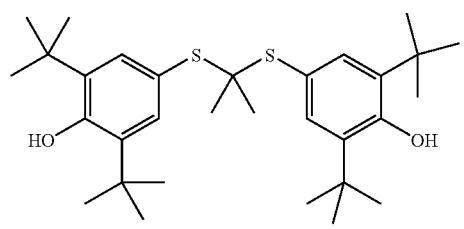

V with a compound of Formula III,

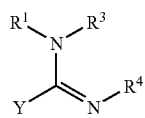

III wherein Y is $R^2$ or $NR^2R^5$;

$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;

$R^1$ and $R^2$ can optionally come together to form a ring;

$R^3$ and $R^4$ can optionally come together to form a ring;

and a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more substituents selected from the group consisting of protected hydroxy, alkyl, alkenyl, acyl, nitro, protected amino, halo, protected carboxy, epoxide and cyano; and separating and isolating said compound of Formula IV.

In a 4th embodiment, the invention is represented by the process to manufacture a compound of Formula I or its ester or salt thereof,

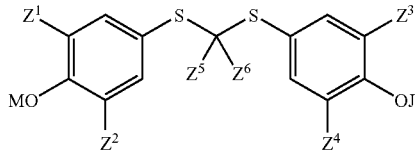

I wherein $Z^1$, $Z^2$, $Z^3$, and $Z^4$ are independently selected from the group consisting of hydrogen and alkyl, said alkyl optionally substituted by hydroxy, alkyl, alkenyl, acyl, nitro, amino, halo, carboxy and cyano;

$Z^5$ and $Z^6$ are the same or different and independently selected from the group consisting of alkyl, alkenyl, and aryl all of which can be optionally substituted by hydroxy, alkyl, alkenyl, acyl, nitro, amino, halo, carboxy and cyano;

$Z^5$ and $Z^6$ can come together to form a carbocyclic ring;

M is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality; and J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

the process comprising:

reacting a compound of Formula II,

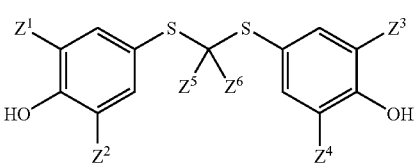

II wherein $Z^1$, $Z^2$, $Z^3$, $Z^4$, $Z^5$ and $Z^6$ are as previously defined, with a compound of Formula III,

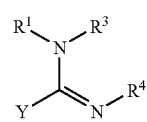

III wherein Y is $R^2$ or $NR^2R^5$;

$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;

$R^1$ and $R^2$ can optionally come together to form a ring;

$R^3$ and $R^4$ can optionally come together to form a ring;

and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; and separating and isolating said compound of Formula I.

In a 5th embodiment, the invention is represented by the process to manufacture a compound of Formula IV or its ester or salt thereof,

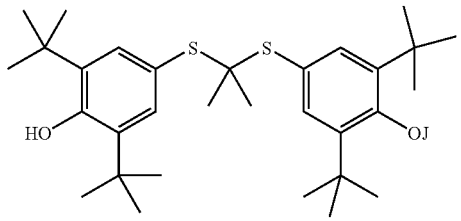

IV wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; the process comprising:

reacting a compound of Formula V,

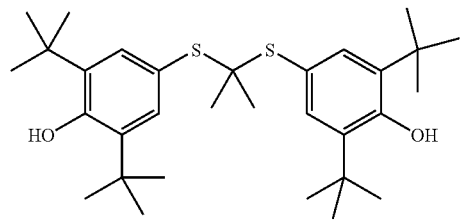

V with a compound of Formula III,

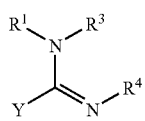

III wherein Y is $R^2$ or $NR^2R^5$;

$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;

$R^1$ and $R^2$ can optionally come together to form a ring;

$R^3$ and $R^4$ can optionally come together to form a ring;

and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; and separating and isolating said compound of Formula IV.

In a 6th embodiment, the invention is represented by the process to manufacture a compound of Formula IV or its ester or salt thereof,

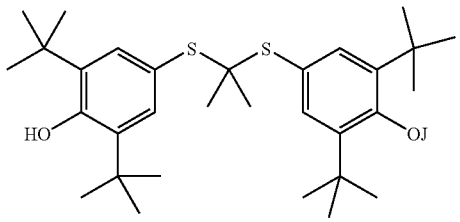

IV wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality; the process comprising:

reacting a compound of Formula V,

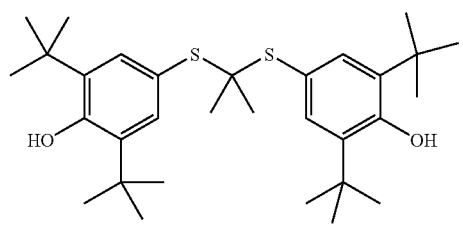

V with a compound of Formula VI,

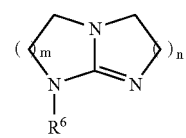

VI wherein $R^6$ is selected from an optionally substituted $C_1$-$C_{10}$ alkyl or an optionally substituted $C_2$-$C_{10}$ alkenyl;

m is an integer selected from 1 to 7;

n is an integer selected from 1 to 7;

and a compound selected from the group consisting of a saturated or unsaturated acyl halide, saturated or unsaturated carboxylic acid anhydride and a saturated or unsaturated activated carboxylic acid ester, all of which may optionally be substituted by one or more selected from the group consisting of protected hydroxy, alkyl, alkenyl, acyl, nitro, protected amino, amino, halo, protected carboxy and cyano; and separating and isolating said compound of Formula IV.

In a 7th embodiment, the invention is represented by the process to manufacture a compound of Formula IV or its ester or salt thereof,

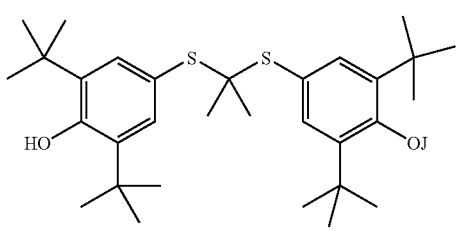

IV wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

the process comprising:

reacting a compound of Formula V,

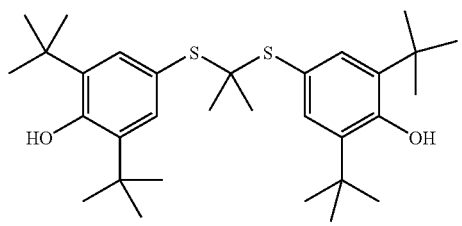

V with a compound of Formula VII,

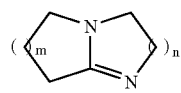

VII wherein m is an integer selected from 1 to 7;
n is an integer selected from 1 to 7;

and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; and separating and isolating said compound of Formula IV.

In an 8th embodiment, the invention is represented by the process to manufacture a compound of Formula IV or its ester or salt thereof,

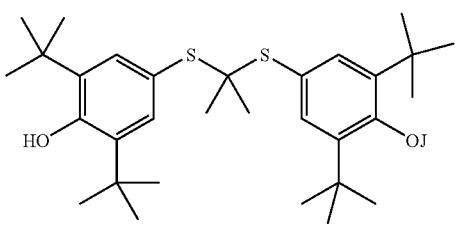

IV wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

the process comprising:

reacting a compound of Formula V,

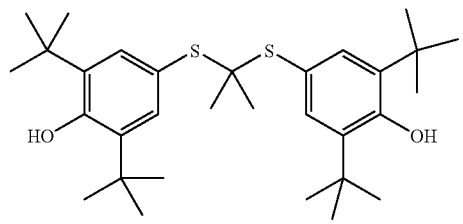

V with a compound of Formula VII,

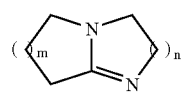

VII wherein m is an integer selected from 1 to 7;
n is an integer selected from 1 to 7;

and a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more substituents selected from the group consisting of protected hydroxy, alkyl, alkenyl, acyl, nitro, protected amino, halo, protected carboxy and cyano; and separating and isolating said compound of Formula IV.

In a 9th embodiment, the invention is represented by the process to manufacture a compound of Formula VIII, IX or X or its ester or salt thereof,

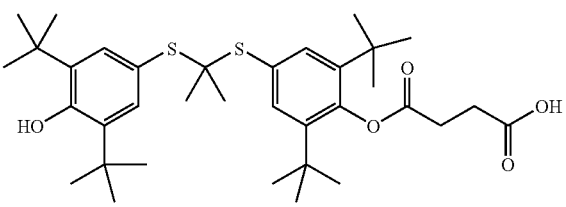

VIII

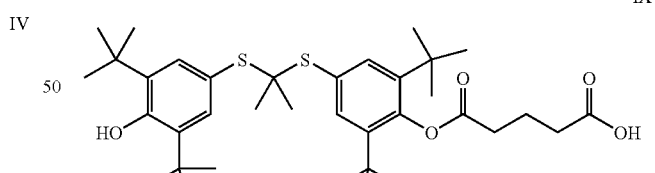

IX

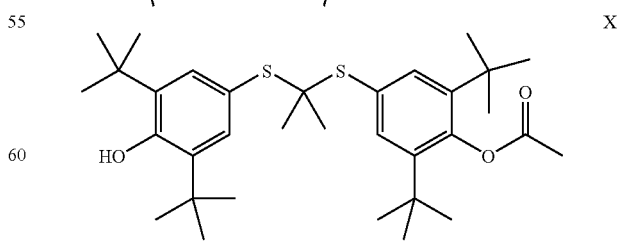

X the process comprising:
reacting a compound of Formula V,

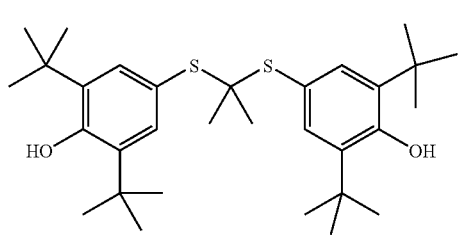

with a compound of Formula VII,

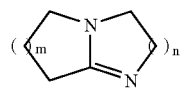

VII wherein m is an integer selected from 1 to 7;
n is an integer selected from 1 to 7;

and a compound selected from the group consisting of succinic acid anhydride, glutaric acid anhydride, and acetic acid anhydride, all of which may optionally be substituted by one or more substituents selected from the group consisting of protected hydroxy, alkyl, alkenyl, acyl, nitro, protected amino, halo, protected carboxy and cyano; and separating and isolating said compound of Formula VIII, IX or X.

In a 10$^{th}$ embodiment, the invention is represented by the process to manufacture a compound of Formula VIII, IX or X or its ester or salt thereof,

VIII

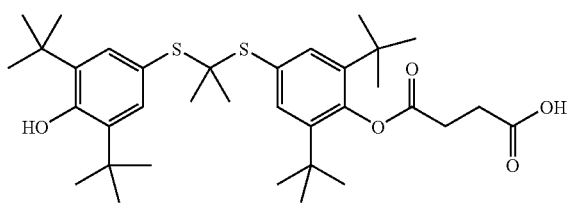

IX

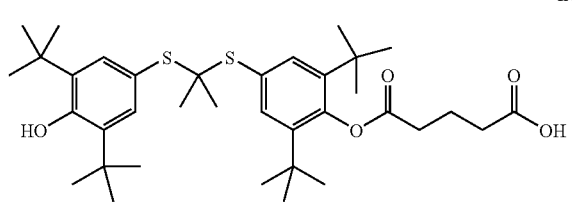

X

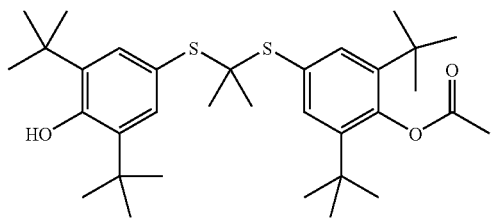

the process comprising:
reacting a compound of Formula V,

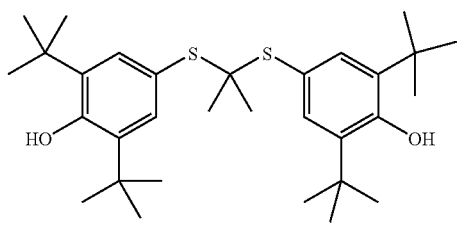

with a compound of Formula DBU or DBN,

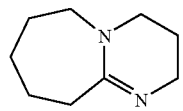

DBU

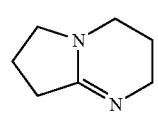

DBN and a compound selected from the group consisting of succinic acid anhydride, glutaric acid anhydride, and acetic acid anhydride, all of which may optionally be substituted by one or more substituents selected from the group consisting of protected hydroxy, alkyl, alkenyl, acyl, nitro, protected amino, halo, protected carboxy and cyano; and separating and isolating said compound of Formula VIII, IX or X.

In a 11$^{th}$ embodiment, the invention is represented by the process to manufacture a compound of Formula VIII or its ester or salt thereof,

VIII

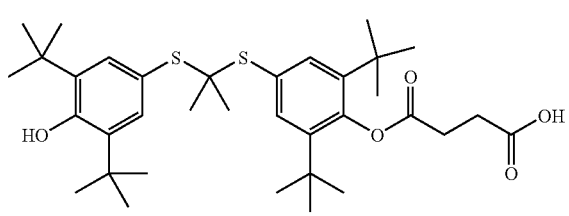

the process comprising:
reacting a compound of Formula V

V

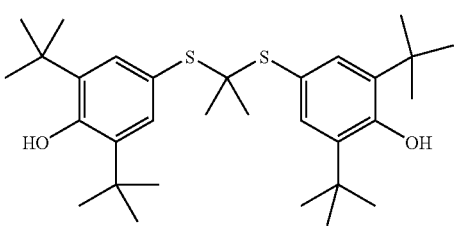

with a compound of Formula DBU,

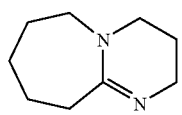
DBU and succinic acid anhydride;

separating and isolating the compound of Formula VIII.

In a 12<sup>th</sup> embodiment, the invention is represented by the process to manufacture a compound of Formula VIII or its ester or salt thereof, VIII
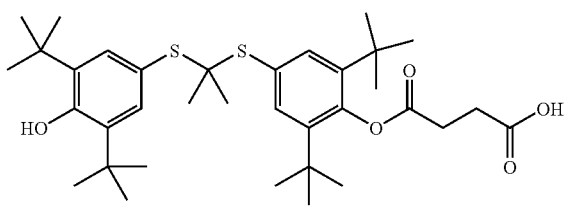

the process comprising:
reacting a compound of Formula V

V
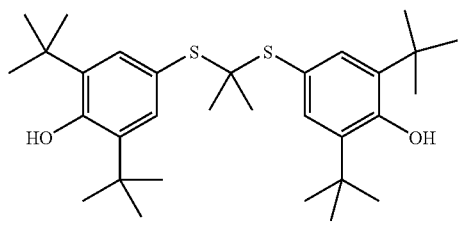

with DBU and succinic acid anhydride;

DBU
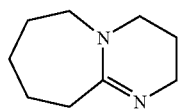

further comprising the addition of an alkaline carbonate; and separating and isolating the compound of Formula VIII.

Further, while compositions and methods are described in terms of "comprising" various components or steps, the compositions and methods can also "consist essentially of" or "consist of" the various components and steps.

Suitable solvents for carrying out the processes of the present disclosure are inert organic solvents, including but are not limited to, alcohols, aldehydes, amides, ethers, esters, halogenated solvents, hydrocarbons, glycols and glycol ethers, ketones, nitriles, and numerous other solvents common in chemical processes, as well as mixtures of such solvents. These inert solvents can be used alone or in combination, and can be miscible or immiscible with each other.

SCHEME

Scheme A as follows illustrates generally the process steps involved in the preparation of the compounds of the present invention. Unless otherwise indicated J, M, $R^1$, $R^2$, $R^3$, $R^4$, $R^5$, Y, $Z^1$, $Z^2$, $Z^3$, $Z^4$, $Z^5$, and $Z^6$ in the reaction Scheme and the discussions that follow are defined as above.

Scheme A

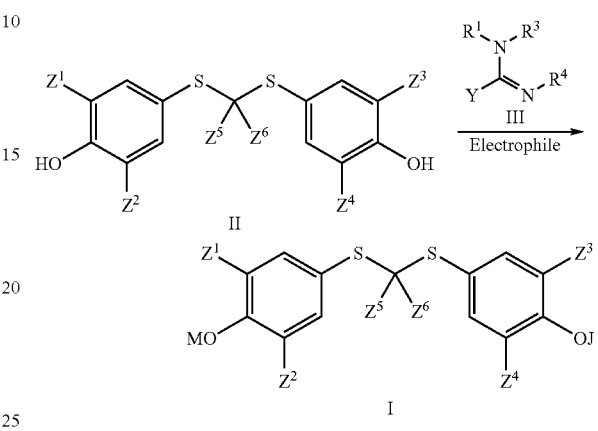

EXAMPLES

The following are non-limiting examples of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

Example 1

In a dry 10 mL round bottom fitted with a nitrogen inlet, thermocouple and stir bar was charged probucol (0.25 g, 0.48 mmol) followed by 2.5 mL anhydrous dimethylformamide. Succinic anhydride (250 mg, 2.50 mmol) was added in 1 portion and the resulting solution was heated to 50° C. 1,8-Diazabicyclo[5.4.0]undec-7-ene (0.300 mL, 2.01 mmol) was added in 1 portion and the reaction was heated for an additional 1 h. Analysis by HPLC of the reaction mixture indicated 42% probucol monosuccinate, 6% probucol disuccinate, and 51% probucol by weight.

Example 2

In a dry 10 mL round bottom fitted with a nitrogen inlet and stir bar was charged probucol (0.25 g, 0.48 mmol) followed by 2.5 mL anhydrous dimethylformamide. Succinic anhydride (250 mg, 2.50 mmol) was added in 1 portion and the resulting solution was aged at room temperature. 1,8-Diazabicyclo[5.4.0]undec-7-ene (0.300 mL, 2.01 mmol) was added in 1 portion and the reaction was aged for an additional 1 h. Analysis by HPLC of the reaction mixture indicated 33% probucol monosuccinate, 5% probucol disuccinate, and 61% probucol by weight.

Example 3

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) was added in 1 portion and the resulting solution was aged at room temperature. 1,8-Diazabicyclo[5.4.0]undec-7-ene (0.300 mL, 2.01 mmol) was added in 1 portion and the reaction was aged for an additional 1 h. Analysis by HPLC of the reaction mixture indicated 34% probucol monosuccinate, 7% probucol disuccinate, and 59% probucol by weight.

Example 4

In a dry 10 mL round bottom fitted with a nitrogen inlet and stir bar was charged probucol (0.25 g, 0.48 mmol) followed by 2.5 mL anhydrous tetrahydrofuran. Succinic anhydride (250 mg, 2.50 mmol) was added in 1 portion and the resulting solution was aged at room temperature. 1,8-Diazabicyclo[5.4.0]undec-7-ene (0.300 mL, 2.01 mmol) was added in 1 portion and the reaction was aged for an additional 1 h. The reaction was slowly quenched with 1 N HCl, diluted with EtOAc and the phases were separated. Analysis by HPLC of the organic layer indicated 40% probucol monosuccinate, 8% probucol disuccinate, and 51% probucol by weight.

Example 5

In a dry 10 mL round bottom fitted with a nitrogen inlet and stir bar was charged probucol (0.25 g, 0.48 mmol) followed by 2.5 mL anhydrous 1,4-dioxane. Succinic anhydride (250 mg, 2.50 mmol) was added in 1 portion and the resulting solution was aged at room temperature. 1,8-Diazabicyclo[5.4.0]undec-7-ene (0.300 mL, 2.01 mmol) was added in 1 portion and the reaction was aged for an additional 1 h. The reaction was slowly quenched with 1 N HCl, diluted with EtOAc and the phases were separated. Analysis by HPLC of the organic layer indicated 41% probucol monosuccinate, 16% probucol disuccinate, and 43% probucol by weight.

Example 6

In a dry 10 mL round bottom fitted with a nitrogen inlet and stir bar was charged probucol (0.25 g, 0.48 mmol) followed by 2.5 mL anhydrous toluene. Succinic anhydride (250 mg, 2.50 mmol) was added in 1 portion and the resulting solution was aged at room temperature. 1,8-Diazabicyclo[5.4.0]undec-7-ene (0.300 mL, 2.01 mmol) was added in 1 portion and the reaction was aged for an additional 1 h. The reaction was slowly quenched with 1 N HCl, diluted with EtOAc and the phases were separated. Analysis by HPLC of the organic layer indicated 32% probucol monosuccinate, 4% probucol disuccinate, and 64% probucol by weight.

Example 7

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) was added in 1 portion and the resulting solution was aged at room temperature. 1,8-Diazabicyclo[5.4.0]undec-7-ene (0.075 mL, 0.50 mmol) was added in 1 portion and the reaction was aged for an additional 1 h. Analysis by HPLC of the reaction mixture indicated 15% probucol monosuccinate, 1% probucol disuccinate, and 83% probucol by weight.

Example 8

In a dry 10 mL round bottom fitted with a nitrogen inlet, thermocouple and stir bar was charged probucol (0.25 g, 0.48 mmol) followed by 2.5 mL anhydrous acetonitrile. Succinic anhydride (250 mg, 2.50 mmol) was added in 1 portion and the resulting solution was heated to 50° C. 1,8-Diazabicyclo[5.4.0]undec-7-ene (0.075 mL, 0.50 mmol) was added in 1 portion and the reaction was heated for an additional 1 h. Analysis by HPLC of the reaction mixture indicated 20% probucol monosuccinate, 1% probucol disuccinate, and 79% probucol by weight.

Example 9

In a dry 10 mL round bottom fitted with a nitrogen inlet, thermocouple and stir bar was charged probucol (0.25 g, 0.48 mmol) followed by 2.5 mL anhydrous acetonitrile. Succinic anhydride (250 mg, 2.50 mmol) was added in 1 portion and the resulting solution was heated to 50° C. 1,8-Diazabicyclo[5.4.0]undec-7-ene (0.150 mL, 1.00 mmol) was added in 1 portion and the reaction was heated for an additional 1 h. Analysis by HPLC of the reaction mixture indicated 38% probucol monosuccinate, 7% probucol disuccinate, and 55% probucol by weight.

Example 10

In a dry 10 mL round bottom fitted with a nitrogen inlet and stir bar was charged probucol (0.25 g, 0.48 mmol) followed by 2.5 mL anhydrous dimethylformamide. Succinic anhydride (250 mg, 2.50 mmol) was added in 1 portion and the resulting solution was aged at room temperature. 1,8-Diazabicyclo[5.4.0]undec-7-ene (0.075 mL, 0.50 mmol) was added in 1 portion and the reaction was aged for an additional 45 min. Analysis by HPLC of the reaction mixture indicated 12% probucol monosuccinate, 1% probucol disuccinate, and 87% probucol by weight.

Example 11

In a dry 10 mL round bottom fitted with a nitrogen inlet and stir bar was charged probucol (0.25 g, 0.48 mmol) followed by 2.5 mL anhydrous tetrahydrofuran. Succinic anhydride (250 mg, 2.50 mmol) was added in 1 portion and the resulting solution was aged at room temperature. 1,8-Diazabicyclo[5.4.0]undec-7-ene (0.075 mL, 0.50 mmol) was added in 1 portion and the reaction was aged for an additional 45 min. The reaction was slowly quenched with 1 N HCl, diluted with EtOAc and NaCl and the phases were separated. Analysis by HPLC of the organic layer indicated 22% probucol monosuccinate, 2% probucol disuccinate, and 76% probucol by weight.

Example 12

In a dry 10 mL round bottom fitted with a nitrogen inlet and stir bar was charged probucol (0.25 g, 0.48 mmol) followed by 2.5 mL anhydrous 1,4-dioxane. Succinic anhydride (250 mg, 2.50 mmol) was added in 1 portion and the resulting solution was aged at room temperature. 1,8-Diazabicyclo[5.4.0]undec-7-ene (0.075 mL, 0.50 mmol) was added in 1 portion and the reaction was aged for an additional 45 min. The reaction was slowly quenched with 1 N HCl, diluted with EtOAc and NaCl and the phases were separated. Analysis by HPLC of the organic layer indicated 24% probucol monosuccinate, 3% probucol disuccinate, and 73% probucol by weight.

Example 13

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) was added in 1 portion and the resulting solution was aged at room temperature. 1,8-Diazabicyclo[5.4.0]undec-7-ene (0.150 mL, 1.00 mmol) was added in 1 portion and the reaction was aged for an additional 15 min. Analysis by HPLC of the reaction mixture indicated 25% probucol monosuccinate, 2% probucol disuccinate, and 73% probucol by weight.

Example 14

In a dry 10 mL round bottom fitted with a nitrogen inlet, thermocouple and stir bar was charged probucol (0.25 g, 0.48 mmol) followed by 2.5 mL anhydrous tetrahydrofuran. Succinic anhydride (250 mg, 2.50 mmol) was added in 1 portion and the resulting solution was heated to 50° C. 1,8-Diazabicyclo[5.4.0]undec-7-ene (0.150 mL, 1.00 mmol) was added in 1 portion and the reaction was heated for an additional 15 min. Analysis by HPLC of the reaction mixture indicated 29% probucol monosuccinate, 3% probucol disuccinate, and 68% probucol by weight.

Example 15

In a dry 10 mL round bottom fitted with a nitrogen inlet, thermocouple and stir bar was charged probucol (0.25 g, 0.48 mmol) followed by 2.5 mL anhydrous dimethylformamide. Succinic anhydride (250 mg, 2.50 mmol) was added in 1 portion and the resulting solution was heated to 50° C. 1,8-Diazabicyclo[5.4.0]undec-7-ene (0.150 mL, 1.00 mmol) was added in 1 portion and the reaction was heated for an additional 15 min. Analysis by HPLC of the reaction mixture indicated 28% probucol monosuccinate, 3% probucol disuccinate, and 69% probucol by weight.

Example 16

In a dry 10 mL round bottom fitted with a nitrogen inlet and stir bar was charged probucol (0.25 g, 0.48 mmol) followed by 2.5 mL anhydrous dimethylformamide. 1,8-Diazabicyclo[5.4.0]undec-7-ene (0.150 mL, 1.00 mmol) was added in 1 portion and the resulting solution was aged at room temperature. Succinic anhydride (250 mg, 2.50 mmol) was added in 1 portion and the reaction was aged overnight. Analysis by HPLC of the reaction mixture indicated 25% probucol monosuccinate, 2% probucol disuccinate, and 73% probucol by weight.

Example 17

In a dry 10 mL round bottom fitted with a nitrogen inlet, thermocouple and stir bar was charged probucol (0.25 g, 0.48 mmol) followed by 2.5 mL anhydrous dimethylformamide. 1,8-Diazabicyclo[5.4.0]undec-7-ene (0.150 mL, 1.00 mmol) was added in 1 portion and the resulting solution was heated to 50° C. Succinic anhydride (250 mg, 2.50 mmol) was added in 1 portion and the reaction was heated overnight. Analysis by HPLC of the reaction mixture indicated 26% probucol monosuccinate, 2% probucol disuccinate, and 72% probucol by weight.

Example 18

In a dry 10 mL round bottom fitted with a nitrogen inlet and stir bar was charged probucol (0.25 g, 0.48 mmol) followed by 2.5 mL anhydrous acetonitrile. 1,8-Diazabicyclo[5.4.0]undec-7-ene (0.150 mL, 1.00 mmol) was added in 1 portion followed by an additional 2.5 mL of acetonitrile and the resulting solution was aged at room temperature. Succinic anhydride (250 mg, 2.50 mmol) was added in 1 portion and the reaction was aged overnight. Analysis by HPLC of the reaction mixture indicated 37% probucol monosuccinate, 8% probucol disuccinate, and 55% probucol by weight.

Example 19

In a dry 10 mL round bottom fitted with a nitrogen inlet, thermocouple and stir bar was charged probucol (0.25 g, 0.48 mmol) followed by 2.5 mL anhydrous acetonitrile. 1,8-Diazabicyclo[5.4.0]undec-7-ene (0.150 mL, 1.00 mmol) was added in 1 portion and the resulting solution was heated to 50° C. Succinic anhydride (250 mg, 2.50 mmol) was added in 1 portion and the reaction was heated overnight. Analysis by HPLC of the reaction mixture indicated 44% probucol monosuccinate, 10% probucol disuccinate, and 46% probucol by weight.

Example 20

In a dry 10 mL round bottom fitted with a nitrogen inlet and stir bar was charged probucol (0.25 g, 0.48 mmol) followed by 2.5 mL anhydrous dimethylformamide. 1,8-Diazabicyclo[5.4.0]undec-7-ene (0.300 mL, 2.01 mmol) was added in 1 portion and the resulting solution was aged at room temperature. Succinic anhydride (250 mg, 2.50 mmol) was added in 1 portion and the reaction was aged overnight. Analysis by HPLC of the reaction mixture indicated 40% probucol monosuccinate, 9% probucol disuccinate, and 51% probucol by weight.

Example 21

In a dry 10 mL round bottom fitted with a nitrogen inlet and stir bar was charged probucol (0.25 g, 0.48 mmol) followed by 5.0 mL anhydrous acetonitrile. 1,8-Diazabicyclo[5.4.0]undec-7-ene (0.150 mL, 1.00 mmol) was added in 1 portion and the resulting solution was aged at room temperature. Succinic anhydride (250 mg, 2.50 mmol) was added in 1 portion and the reaction was aged overnight. Analysis by HPLC of the reaction mixture indicated 43% probucol monosuccinate, 12% probucol disuccinate, and 45% probucol by weight.

Example 22

In a dry 10 mL round bottom fitted with a nitrogen inlet and stir bar was charged probucol (0.25 g, 0.48 mmol) followed by 0.25 mL 1,1,3,3-tetramethylurea and 2.5 mL anhydrous acetonitrile. 1,8-Diazabicyclo[5.4.0]undec-7-ene (0.150 mL, 1.00 mmol) was added in 1 portion and the resulting solution was aged at room temperature. Succinic anhydride (250 mg, 2.50 mmol) was added in 1 portion and the reaction was aged for an additional 2 h. Analysis by HPLC of the reaction mixture indicated 43% probucol monosuccinate, 11% probucol disuccinate, and 46% probucol by weight.

Example 23

In a dry 10 mL round bottom fitted with a nitrogen inlet and stir bar was charged probucol (0.25 g, 0.48 mmol) followed by 0.25 mL 1,1,3,3-tetramethylurea and 2.5 mL anhydrous acetonitrile. 1,8-Diazabicyclo[5.4.0]undec-7-ene (0.150 mL, 1.00 mmol) was added in 1 portion and the resulting solution was aged at 50° C. Succinic anhydride (250 mg, 2.50 mmol) was added in 1 portion and the reaction was heated for an additional 2 h. Analysis by HPLC of the reaction mixture indicated 48% probucol monosuccinate, 15% probucol disuccinate, and 37% probucol by weight.

Example 24

In a dry 10 mL round bottom fitted with a nitrogen inlet and stir bar was charged probucol (0.25 g, 0.48 mmol) followed by 0.25 mL 1,1,3,3-tetramethylurea and 2.5 mL anhydrous dimethylformamide. 1,8-Diazabicyclo[5.4.0]undec-7-ene (0.150 mL, 1.00 mmol) was added in 1 portion and the resulting solution was aged at 50° C. Succinic anhydride (250 mg, 2.50 mmol) was added in 1 portion and the reaction was heated for an additional 2 h. Analysis by HPLC of the reaction mixture indicated 34% probucol monosuccinate, 4% probucol disuccinate, and 62% probucol by weight.

Example 25

In a dry 10 mL round bottom fitted with a nitrogen inlet and stir bar was charged probucol (0.25 g, 0.48 mmol) followed by 0.25 mL 1,1,3,3-tetramethylurea and 2.5 mL anhydrous 1,4-dioxane. 1,8-Diazabicyclo[5.4.0]undec-7-ene (0.150 mL, 1.00 mmol) was added in 1 portion and the resulting solution was aged at room temperature. Succinic anhydride (250 mg, 2.50 mmol) was added in 1 portion and the reaction was aged for an additional 2 h. The reaction was slowly quenched with 1 N HCl, diluted with EtOAc and the phases were separated. Analysis by HPLC of the organic layer indicated 41% probucol monosuccinate, 13% probucol disuccinate, and 46% probucol by weight.

Example 26

In a dry 10 mL round bottom fitted with a nitrogen inlet and stir bar was charged probucol (0.25 g, 0.48 mmol) followed by 0.25 mL 1,1,3,3-tetramethylurea and 2.5 mL anhydrous tetrahydrofuran. 1,8-Diazabicyclo[5.4.0]undec-7-ene (0.150 mL, 1.00 mmol) was added in 1 portion and the resulting solution was aged at room temperature. Succinic anhydride (250 mg, 2.50 mmol) was added in 1 portion and the reaction was aged for an additional 2 h. The reaction was slowly quenched with 1 N HCl, diluted with EtOAc and the phases were separated. Analysis by HPLC of the organic layer indicated 45% probucol monosuccinate, 15% probucol disuccinate, and 40% probucol by weight.

Example 27

In a dry 10 mL round bottom fitted with a nitrogen inlet and stir bar was charged probucol (0.25 g, 0.48 mmol) followed by 0.25 mL 1,1,3,3-tetramethylurea and 1.0 mL anhydrous acetonitrile. 1,8-Diazabicyclo[5.4.0]undec-7-ene (0.150 mL, 1.00 mmol) was added in 1 portion and the resulting solution was aged at room temperature. Succinic anhydride (250 mg, 2.50 mmol) was added in 1 portion and the reaction was aged for an additional 2 h. Analysis by HPLC of the reaction mixture indicated 45% probucol monosuccinate, 13% probucol disuccinate, and 42% probucol by weight.

Example 28

In a dry 10 mL round bottom fitted with a nitrogen inlet and stir bar was charged probucol (0.25 g, 0.48 mmol) followed by 0.25 mL 1,1,3,3-tetramethylurea and 2.5 mL anhydrous 1,4-dioxane. 1,8-Diazabicyclo[5.4.0]undec-7-ene (0.150 mL, 1.00 mmol) was added in 1 portion and the resulting solution was aged at 50° C. Succinic anhydride (250 mg, 2.50 mmol) was added in 1 portion and the reaction was heated for an additional 2 h. Analysis by HPLC of the reaction mixture indicated 42% probucol monosuccinate, 10% probucol disuccinate, and 48% probucol by weight.

Example 29

In a dry 10 mL round bottom fitted with a nitrogen inlet and stir bar was charged probucol (0.25 g, 0.48 mmol) followed by 0.25 mL 1,1,3,3-tetramethylurea and 2.5 mL anhydrous tetrahydrofuran. 1,8-Diazabicyclo[5.4.0]undec-7-ene (0.150 mL, 1.00 mmol) was added in 1 portion and the resulting solution was aged at 50° C. Succinic anhydride (250 mg, 2.50 mmol) was added in 1 portion and the reaction was heated for an additional 2 h. Analysis by HPLC of the reaction mixture indicated 43% probucol monosuccinate, 8% probucol disuccinate, and 49% probucol by weight.

Example 30

In a dry 10 mL round bottom fitted with a nitrogen inlet and stir bar was charged probucol (0.25 g, 0.48 mmol) followed by 0.25 mL 1,1,3,3-tetramethylurea and 1,8-Diazabicyclo[5.4.0]undec-7-ene (0.300 mL, 2.01 mmol) was added in 1 portion. To the reaction mixture was added 2.5 mL anhydrous acetone and the resulting solution was aged at room temperature. Succinic anhydride (250 mg, 2.50 mmol) was added in 1 portion and the reaction was aged for an additional 2 h. Analysis by HPLC of the reaction mixture indicated 32% probucol monosuccinate, 5% probucol disuccinate, and 63% probucol by weight.

Example 31

In a dry 10 mL round bottom fitted with a nitrogen inlet and stir bar was charged probucol (0.25 g, 0.48 mmol) followed by 0.25 mL 1,1,3,3-tetramethylurea and 5.0 mL anhydrous acetonitrile. 1,8-Diazabicyclo[5.4.0]undec-7-ene (0.300 mL, 2.01 mmol) was added in 1 portion and the resulting solution was aged at room temperature. Succinic anhydride (250 mg, 2.50 mmol) was added in 1 portion and the reaction was aged for an additional 2 h. Analysis by HPLC of the reaction mixture indicated 44% probucol monosuccinate, 12% probucol disuccinate, and 44% probucol by weight.

Example 32

In a dry 10 mL round bottom fitted with a nitrogen inlet and stir bar was charged probucol (0.25 g, 0.48 mmol) followed by 0.50 mL 1,1,3,3-tetramethylurea and 2.5 mL anhydrous acetonitrile. 1,8-Diazabicyclo[5.4.0]undec-7-ene (0.300 mL, 2.01 mmol) was added in 1 portion and the resulting solution was aged at room temperature. Succinic anhydride (250 mg, 2.50 mmol) was added in 1 portion and the reaction was aged for an additional 2 h. Analysis by HPLC of the reaction mixture indicated 41% probucol monosuccinate, 9% probucol disuccinate, and 50% probucol by weight.

Example 33

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) was added in 1 portion and the resulting solution was aged at room temperature. 1,8-Diazabicyclo[5.4.0]undec-7-ene (0.600 mL, 4.01 mmol) was added in 1 portion and the resulting solution was aged for an additional 1 h. Analysis by HPLC of the reaction mixture indicated 27% probucol monosuccinate, 5% probucol disuccinate, and 68% probucol by weight.

Example 34

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) was added in 1 portion and the resulting solution was heated to 50° C. 1,8-Diazabicyclo[5.4.0]undec-7-ene (0.600 µL, 4.01 mmol) was added in 1 portion and the resulting solution was heated for an additional 1 h. Analysis by HPLC of the reaction mixture indicated 45% probucol monosuccinate, 5% probucol disuccinate, and 50% probucol by weight.

Example 35

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) was added in 1 portion and the resulting solution was heated to 50° C. 1,8-Diazabicyclo[5.4.0]undec-7-ene (0.300 mL, 2.01 mmol) was added in 1 portion and the resulting solution was heated for an additional 1 h. Analysis by HPLC of the reaction mixture indicated 49% probucol monosuccinate, 18% probucol disuccinate, and 33% probucol by weight.

Example 36

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) and 4-(dimethylamino)pyridine (60 mg, 0.49 mmol) were added and the resulting solution was heated to 50° C. 1,8-Diazabicyclo[5.4.0]undec-7-ene (0.300 mL, 2.01 mmol) was added in 1 portion and the resulting solution was heated for an additional 1 h. Analysis by HPLC of the reaction mixture indicated 49% probucol monosuccinate, 20% probucol disuccinate, and 31% probucol by weight.

Example 37

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) and 4-(dimethylamino)pyridine (250 mg, 2.05 mmol) were added and the resulting solution was heated to 50° C. 1,8-Diazabicyclo[5.4.0]undec-7-ene (0.075 mL, 0.50 mmol) was added in 1 portion and the resulting solution was heated for an additional 1 h. Analysis by HPLC of the reaction mixture indicated 25% probucol monosuccinate, 2% probucol disuccinate, and 73% probucol by weight.

Example 38

In a dry 10 mL round bottom fitted with a nitrogen inlet and stir bar was charged probucol (0.25 g, 0.48 mmol) followed by 2.5 mL anhydrous acetonitrile. Succinic anhydride (150 mg, 1.50 mmol) was added in 1 portion and the resulting solution was heated to 50° C. 1,8-Diazabicyclo[5.4.0]undec-7-ene (0.225 mL, 1.50 mmol) was added in 1 portion and the resulting solution was heated for an additional 2 h. Analysis by HPLC of the reaction mixture indicated 46% probucol monosuccinate, 11% probucol disuccinate, and 42% probucol by weight.

Example 39

In a dry 10 mL round bottom fitted with a nitrogen inlet and stir bar was charged probucol (0.25 g, 0.48 mmol) followed by 2.5 mL anhydrous acetonitrile. Succinic anhydride (250 mg, 2.50 mmol) was added in 1 portion and the resulting solution was heated to 50° C. 1,8-Diazabicyclo[5.4.0]undec-7-ene (0.225 mL, 1.50 mmol) was added in 1 portion and the resulting solution was heated for an additional 2 h. Analysis by HPLC of the reaction mixture indicated 46% probucol monosuccinate, 14% probucol disuccinate, and 40% probucol by weight.

Example 40

In a dry 10 mL round bottom fitted with a nitrogen inlet and stir bar was charged probucol (0.25 g, 0.48 mmol) followed by 2.5 mL anhydrous acetonitrile. Succinic anhydride (150 mg, 1.50 mmol) was added in 1 portion and the resulting solution was heated to 50° C. 1,8-Diazabicyclo[5.4.0]undec-7-ene (0.300 mL, 2.01 mmol) was added in 1 portion and the resulting solution was heated for an additional 2 h. Analysis by HPLC of the reaction mixture indicated 49% probucol monosuccinate, 10% probucol disuccinate, and 41% probucol by weight.

Example 41

In a dry 10 mL round bottom fitted with a nitrogen inlet and stir bar was charged probucol (0.25 g, 0.48 mmol) followed by 2.5 mL anhydrous acetonitrile. Succinic anhydride (150 mg, 1.50 mmol) was added in 1 portion and the resulting solution was heated to 50° C. 1,8-Diazabicyclo[5.4.0]undec-7-ene (0.150 mL, 1.00 mmol) was added in 1 portion and the resulting solution was heated for an additional 2 h. Analysis by HPLC of the reaction mixture indicated 44% probucol monosuccinate, 11% probucol disuccinate, and 45% probucol by weight.

Example 42

In a dry 10 mL round bottom fitted with a nitrogen inlet and stir bar was charged probucol (0.25 g, 0.48 mmol) followed by 2.5 mL anhydrous acetonitrile. Succinic anhydride (75 mg, 0.75 mmol) was added in 1 portion and the resulting solution was heated to 50° C. 1,8-Diazabicyclo[5.4.0]undec-7-ene (0.150 mL, 1.00 mmol) was added in 1 portion and the resulting solution was heated for an additional 2 h. Analysis by HPLC of the reaction mixture indicated 36% probucol monosuccinate, 5% probucol disuccinate, and 59% probucol by weight.

Example 43

In a dry 10 mL round bottom fitted with a nitrogen inlet and stir bar was charged probucol (0.25 g, 0.48 mmol) followed by 2.5 mL anhydrous acetonitrile. Succinic anhydride (75 mg, 0.75 mmol) was added in 1 portion and the resulting solution was heated to 50° C. 1,8-Diazabicyclo[5.4.0]undec-7-ene (0.225 mL, 1.50 mmol) was added in 1 portion and the resulting solution was heated for an additional 2 h. Analysis by HPLC of the reaction mixture indicated 35% probucol monosuccinate, 3% probucol disuccinate, and 62% probucol by weight.

Example 44

In a dry 10 mL round bottom fitted with a nitrogen inlet and stir bar was charged probucol (0.25 g, 0.48 mmol), succinic anhydride (250 mg, 2.50 mmol), and $K_2CO_3$ (140 mg, 1.01 mmol) followed by 2.5 mL anhydrous dimethylformamide. The resulting reaction mixture was charged with 1,8-diazabicyclo[5.4.0]undec-7-ene (0.025 mL, 0.17 mmol) and aged overnight. Analysis by HPLC of the reaction mixture indicated 11% probucol monosuccinate, 1% probucol disuccinate, and 88% probucol by weight.

Example 45

In a dry 10 mL round bottom fitted with a nitrogen inlet and stir bar was charged probucol (0.25 g, 0.48 mmol), succinic anhydride (250 mg, 2.50 mmol), and $Cs_2CO_3$ (330 mg, 1.01 mmol) followed by 2.5 mL anhydrous dimethylformamide. The resulting reaction mixture was charged with 1,8-diazabicyclo[5.4.0]undec-7-ene (0.025 mL, 0.17 mmol) and aged overnight. Analysis by HPLC of the reaction mixture indicated 25% probucol monosuccinate, 2% probucol disuccinate, and 73% probucol by weight.

Example 46

In a dry 10 mL round bottom fitted with a nitrogen inlet and stir bar was charged probucol (0.25 g, 0.48 mmol), succinic anhydride (250 mg, 2.50 mmol), and $K_2CO_3$ (140 mg, 1.01 mmol) followed by 2.5 mL anhydrous acetonitrile. The resulting reaction mixture was charged with 1,8-diazabicyclo[5.4.0]undec-7-ene (0.025 mL, 0.17 mmol) and aged overnight. Analysis by HPLC of the reaction mixture indicated 7% probucol monosuccinate, <1% probucol disuccinate, and 93% probucol by weight.

Example 47

In a dry 10 mL round bottom fitted with a nitrogen inlet and stir bar was charged probucol (0.25 g, 0.48 mmol), succinic anhydride (250 mg, 2.50 mmol), and $Cs_2CO_3$ (330 mg, 1.01 mmol) followed by 2.5 mL anhydrous acetonitrile. The resulting reaction mixture was charged with 1,8-diazabicyclo[5.4.0]undec-7-ene (0.025 mL, 0.17 mmol) and aged overnight. Analysis by HPLC of the reaction mixture indicated 7% probucol monosuccinate, <1% probucol disuccinate, and 92% probucol by weight.

Example 48

In a dry 10 mL round bottom fitted with a nitrogen inlet and stir bar was charged probucol (0.25 g, 0.48 mmol), succinic anhydride (250 mg, 2.50 mmol), and $K_2CO_3$ (140 mg, 1.01 mmol) followed by 2.5 mL anhydrous dimethylformamide. The resulting reaction mixture was heated to 50° C. and then charged with 1,8-diazabicyclo[5.4.0]undec-7-ene (0.025 mL, 0.17 mmol) and heated overnight. Analysis by HPLC of the reaction mixture indicated 14% probucol monosuccinate, <1% probucol disuccinate, and 86% probucol by weight.

Example 49

In a dry 10 mL round bottom fitted with a nitrogen inlet and stir bar was charged probucol (0.25 g, 0.48 mmol), succinic anhydride (250 mg, 2.50 mmol), and $Cs_2CO_3$ (330 mg, 1.01 mmol) followed by 2.5 mL anhydrous dimethylformamide. The resulting reaction mixture was heated to 50° C. and then charged with 1,8-diazabicyclo[5.4.0]undec-7-ene (0.025 mL, 0.17 mmol) and heated for an additional 2 h. Analysis by HPLC of the reaction mixture indicated 19% probucol monosuccinate, 1% probucol disuccinate, and 80% probucol by weight.

Example 50

In a dry 10 mL round bottom fitted with a nitrogen inlet and stir bar was charged probucol (0.25 g, 0.48 mmol), succinic anhydride (250 mg, 2.50 mmol), and $K_2CO_3$ (140 mg, 1.01 mmol) followed by 2.5 mL anhydrous acetonitrile. The resulting reaction mixture was heated to 50° C. and then charged with 1,8-diazabicyclo[5.4.0]undec-7-ene (0.025 mL, 0.17 mmol) and heated overnight. Analysis by HPLC of the reaction mixture indicated 28% probucol monosuccinate, 3% probucol disuccinate, and 69% probucol by weight.

Example 51

In a dry 10 mL round bottom fitted with a nitrogen inlet and stir bar was charged probucol (0.25 g, 0.48 mmol), succinic anhydride (250 mg, 2.50 mmol), and $Cs_2CO_3$ (330 mg, 1.01 mmol) followed by 2.5 mL anhydrous acetonitrile. The resulting reaction mixture was heated to 50° C. and then charged with 1,8-diazabicyclo[5.4.0]undec-7-ene (0.025 mL, 0.17 mmol) and heated overnight. Analysis by HPLC of the reaction mixture indicated 40% probucol monosuccinate, 8% probucol disuccinate, and 52% probucol by weight.

Example 52

In a dry 10 mL round bottom fitted with a nitrogen inlet and stir bar was charged probucol (0.25 g, 0.48 mmol) followed by 2.5 mL anhydrous acetonitrile. Succinic anhydride (150 mg, 1.50 mmol) was added and the resulting solution was heated to 50° C. 1,5-Diazabicyclo[4.3.0]non-5-ene (0.180 mL, 0.15 mmol) was added and the solution was heated for an additional 1 h. Analysis by HPLC of the reaction mixture indicated 44% probucol monosuccinate, 9% probucol disuccinate, and 47% probucol by weight.

Example 53

In a dry 10 mL round bottom fitted with a nitrogen inlet and stir bar was charged probucol (0.25 g, 0.48 mmol), succinic anhydride (150 mg, 1.50 mmol), and $Cs_2CO_3$ (330 mg, 1.01 mmol) followed by 2.5 mL anhydrous acetonitrile. The resulting reaction mixture was heated to 50° C. and then charged with 1,8-diazabicyclo[5.4.0]undec-7-ene (0.075 mL, 0.50 mmol) and heated overnight. Analysis by HPLC of the reaction mixture indicated 42% probucol monosuccinate, 9% probucol disuccinate, and 49% probucol by weight.

Example 54

In a dry 10 mL round bottom fitted with a nitrogen inlet and stir bar was charged probucol (0.25 g, 0.48 mmol), succinic anhydride (150 mg, 1.50 mmol), and $Cs_2CO_3$ (330 mg, 1.01 mmol) followed by 2.5 mL anhydrous 2-butanone. The resulting reaction mixture was heated to 50° C. and then charged with 1,8-diazabicyclo[5.4.0]undec-7-ene (0.075 mL, 0.50 mmol) and heated overnight. Analysis by HPLC of the reaction mixture indicated 32% probucol monosuccinate, 4% probucol disuccinate, and 64% probucol by weight.

All of the processes disclosed and claimed herein can be made and executed without undue experimentation in light of the present disclosure. It will be apparent to those of skill in the art that variations may be applied to the methods described herein without departing from the concept and scope of the invention.

What is claimed is:

1. A process of manufacturing a compound of Formula I or its ester or salt thereof,

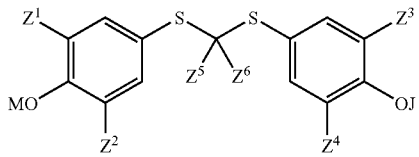

wherein $Z^1$, $Z^2$, $Z^3$, and $Z^4$ are independently selected from the group consisting of hydrogen and alkyl, said alkyl optionally substituted by hydroxy, alkyl, alkenyl, acyl, nitro, amino, halo, carboxy and cyano;

$Z^5$ and $Z^6$ are the same or different and independently selected from the group consisting of alkyl, alkenyl, and aryl all of which can be optionally substituted by hydroxy, alkyl, alkenyl, acyl, nitro, amino, halo, carboxy and cyano;

M is selected from the group consisting of hydrogen, an optionally substituted unsaturated acyl having from 1 to 18 carbon atoms, and an optionally substituted saturated acyl having from 1 to 18 carbon atoms, said optionally substituted unsaturated acyl and optionally substituted saturated acyl optionally containing a polar or charged functionality; and J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

the process comprising:
reacting a compound of Formula II

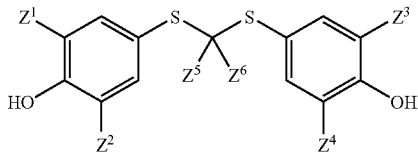

wherein $Z^1$, $Z^2$, $Z^3$, $Z^4$, $Z^5$ and $Z^6$ are as previously defined, with a compound of Formula III,

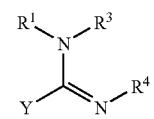

wherein Y is R or $NR^2R^5$;

$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;

$R^1$ and $R^2$ can optionally come together to form a ring;

$R^3$ and $R^4$ can optionally come together to form a ring;

and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; and separating and isolating the compound of Formula I.

2. The process of claim 1 to manufacture a compound of Formula IV or its ester or salt thereof,

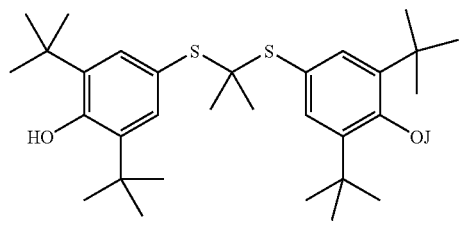

wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

the process comprising:
reacting a compound of Formula V

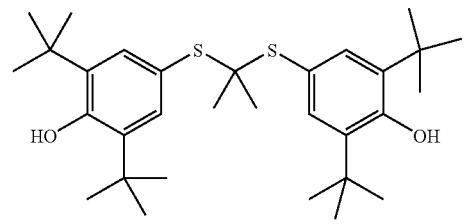

with a compound of Formula III,

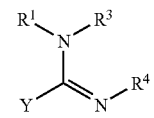

wherein Y is $R^2$ or $NR^2R^5$;

$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;

R¹ and R² can optionally come together to form a ring;
R³ and R⁴ can optionally come together to form a ring;
and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; and
separating and isolating the compound of Formula IV.

3. The process of claim 1 to manufacture a compound of Formula IV or its ester or salt thereof,

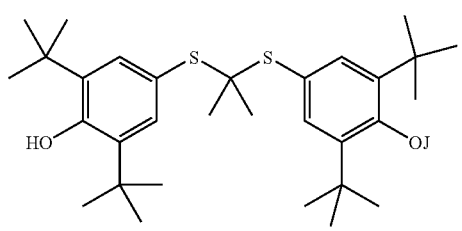

IV wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;
the process comprising:
reacting a compound of Formula V

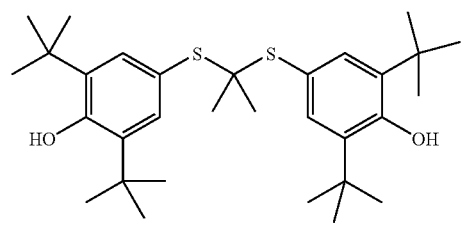

V with a compound of Formula VI,

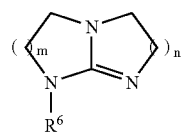

VI wherein R⁶ is selected from an optionally substituted $C_1$-$C_{10}$ alkyl or an optionally substituted $C_2$-$C_{10}$ alkenyl;
m is an integer selected from 1 to 7;
n is an integer selected from 1 to 7;
and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; and
separating and isolating said compound of Formula IV.

4. The process of claim 1 to manufacture a compound of Formula IV or its ester or salt thereof,

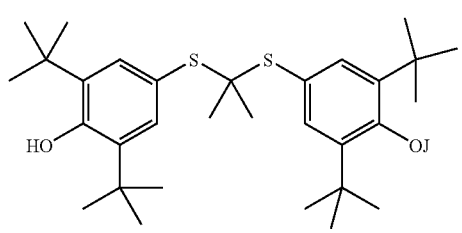

IV wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;
the process comprising:
reacting a compound of Formula V

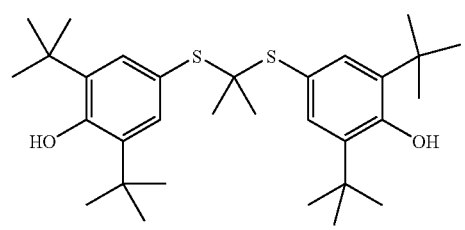

V with a compound of Formula VII,

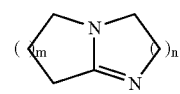

VII wherein m is an integer selected from 1 to 7;
n is an integer selected from 1 to 7;
and a compound selected from the group consisting of a saturated or unsaturated acyl halide, saturated or unsaturated carboxylic acid anhydride and a saturated or unsaturated activated carboxylic acid ester, all of which may optionally be substituted by one or more substituents selected from the group consisting of protected hydroxy, alkyl, alkenyl, acyl, nitro, protected amino, amino, halo, protected carboxy and cyano; and
separating and isolating said compound of Formula IV.

5. The process of claim 1 to manufacture a compound of Formula IV or its ester or salt thereof,

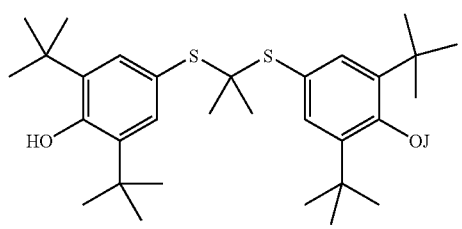

IV wherein J is selected from the group consisting of an optionally substituted unsaturated acyl having from 1 to 18 carbon atoms and an optionally substituted saturated acyl having from 1 to 18 carbon atoms, said optionally substituted unsaturated acyl and optionally substituted saturated acyl optionally containing a polar or charged functionality;

the process comprising:

reacting a compound of Formula V

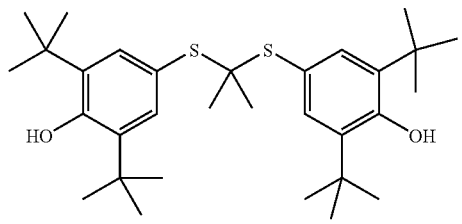

V with a compound of Formula VII,

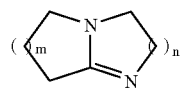

VII wherein m an integer selected from 1 to 7;

n is an integer selected from 1 to 7;

and a compound selected from the group consisting of succinic acid anhydride, glutaric acid anhydride, adipic acid anhydride, suberic acid anhydride, sebacic acid anhydride, azelaic acid anhydride, phthalic acid anhydride, maleic acid anhydride, and acetic acid anhydride, all of which may optionally be substituted by one or more substituents selected from the group consisting of protected hydroxy, alkyl, alkenyl, acyl, nitro, protected amino, halo, protected carboxy and cyano; and separating and isolating said compound of Formula IV.

6. The process of claim 1 to manufacture a compound of Formula VIII, IX or X or its ester or salt thereof,

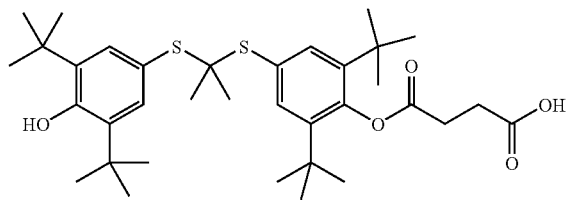

VIII

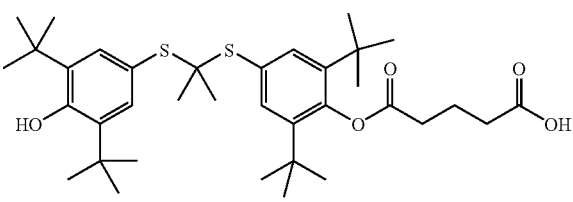

IX

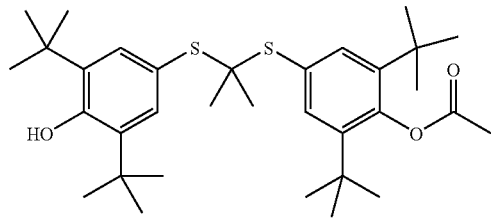

X the process comprising:

reacting a compound of Formula V

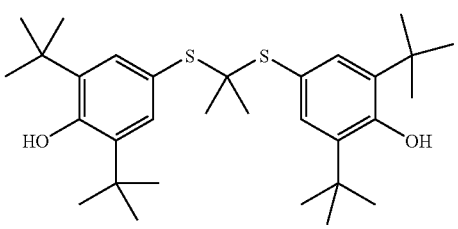

V with a compound of Formula VII,

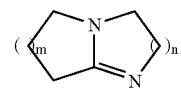

VII wherein m is an integer selected from 1 to 7;

n is an integer selected from 1 to 7;

and a compound selected from the group consisting of succinic acid anhydride, glutaric acid anhydride, and acetic acid anhydride, all of which may optionally be substituted by one or more substituents selected from the group consisting of protected hydroxy, alkyl, alkenyl, acyl, nitro, protected amino, halo, protected carboxy and cyano; and separating and isolating said compound of Formula VIII, IX or X.

7. The process of claim 1 to manufacture a compound of Formula VIII, IX or X or its ester or salt thereof,

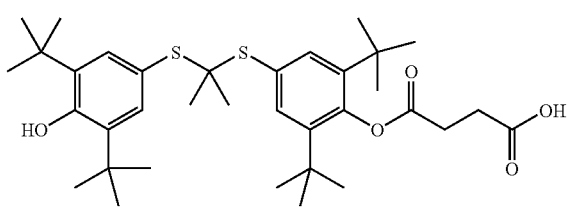

VIII

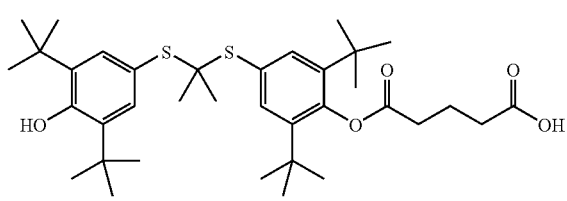

IX

-continued

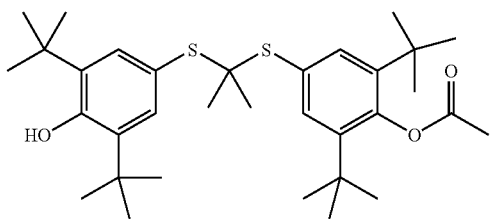

X the process comprising:
reacting a compound of Formula V

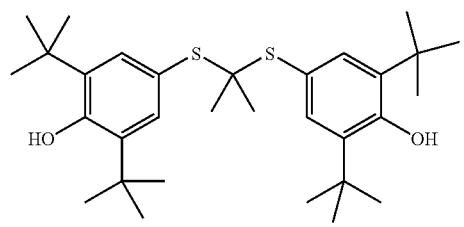

V with a compound of Formula DBU or DBN,

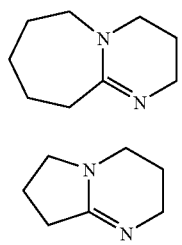

DBU

DBN and a compound selected from the group consisting of succinic acid anhydride, glutaric acid anhydride, and acetic acid anhydride, all of which may optionally be substituted by one or more substituents selected from the group consisting of protected hydroxy, alkyl, alkenyl, acyl, nitro, protected amino, halo, protected carboxy and cyano; and separating and isolating said compound of Formula VIII, IX or X.

8. The process of claim 1 to manufacture a compound of Formula VIII or its ester or salt thereof,

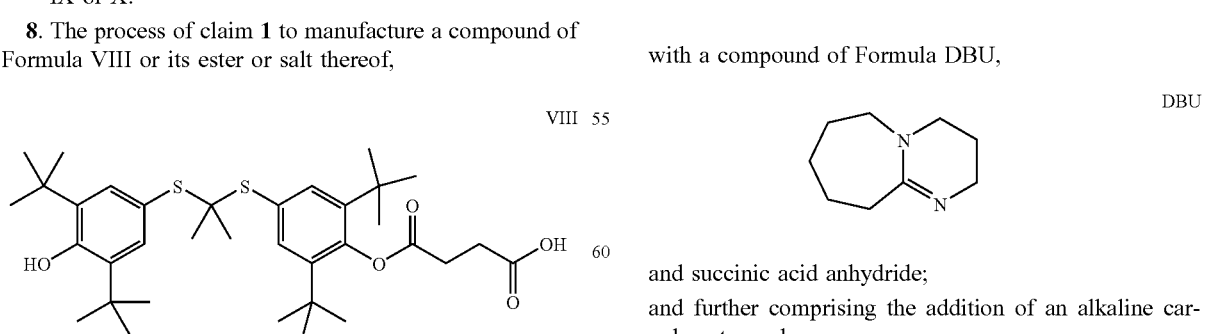

VIII the process comprising:
reacting a compound of Formula V

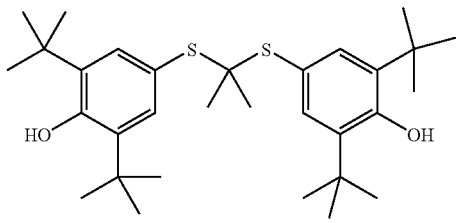

V with a compound of Formula DBU,

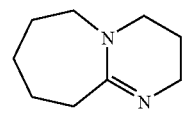

DBU and succinic acid anhydride; and
separating and isolating said compound of Formula VIII.

9. The process of claim 1 to manufacture a compound of Formula VIII or its ester or salt thereof,

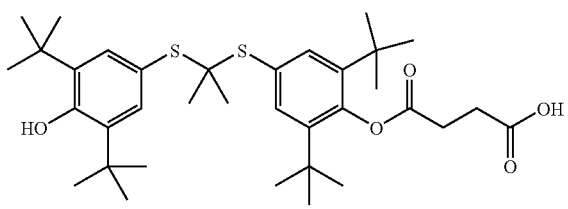

VIII the process comprising:
reacting a compound of Formula V

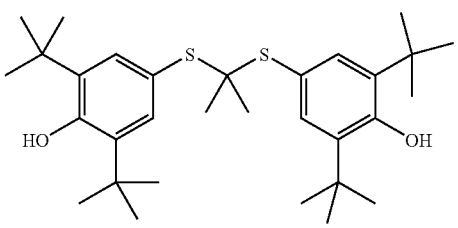

V with a compound of Formula DBU,

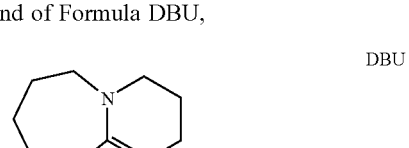

DBU and succinic acid anhydride;
and further comprising the addition of an alkaline carbonate; and
separating and isolating said compound of Formula VIII.

10. A process for manufacturing a compound of Formula I or its ester or salt thereof,

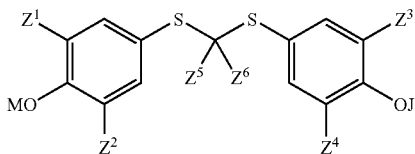

wherein $Z^1$, $Z^2$, $Z^3$, and $Z^4$ are independently selected from the group consisting of hydrogen and alkyl, said alkyl optionally substituted by hydroxy, alkyl, alkenyl, acyl, nitro, amino, halo, carboxy and cyano;

$Z^5$ and $Z^6$ are the same or different and independently selected from the group consisting of alkyl, alkenyl, and aryl all of which can be optionally substituted by hydroxy, alkyl, alkenyl, acyl, nitro, amino, halo, carboxy and cyano;

M is selected from the group consisting of hydrogen, an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality; and J is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

the process comprising:
reacting a compound of Formula II

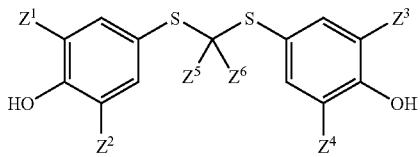

wherein $Z^1$, $Z^2$, $Z^3$, $Z^4$, $Z^5$ and $Z^6$ are as previously defined, with a compound of Formula III,

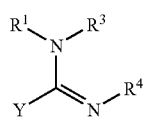

wherein Y is $R^2$ or $NR^2R^5$;
$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;
$R^1$ and $R^2$ can optionally come together to form a ring;
$R^3$ and $R^4$ optionally come together to form a ring;
and a compound selected the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more substituents selected from the group consisting of protected hydroxy, alkyl, alkenyl, acyl, nitro, protected amino, halo, protected carboxy, epoxide and cyano; and separating and isolating the compound of Formula I.

11. The process of claim 10 to manufacture a compound of Formula IV or its ester or salt thereof,

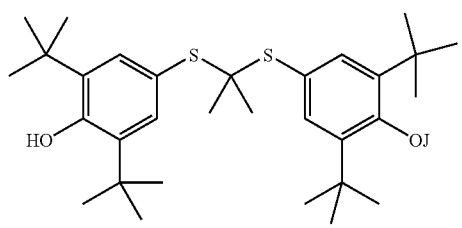

wherein J is selected from the group consisting of an optionally substituted unsaturated alkyl having from 1 to 10 carbon atoms, and an optionally substituted saturated alkyl having from 1 to 10 carbon atoms, said optionally substituted unsaturated alkyl and optionally substituted saturated alkyl optionally containing a polar or charged functionality;

the process comprising:
reacting a compound of Formula V

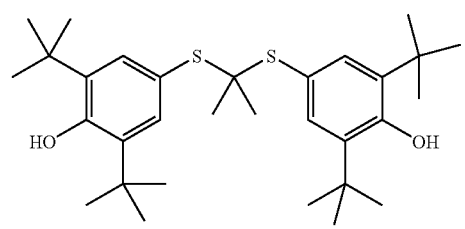

with a compound of Formula III,

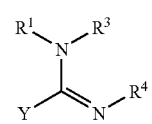

wherein Y is $R^2$ $NR^2R^5$.
$R^1$, $R^2$, $R^3$ and $R^4$ and $R^5$ are independently selected from an optionally substituted $C_1$-$C_{10}$ alkyl or an optionally substituted $C_2$-$C_{10}$ alkenyl;
$R^1$ and $R^2$ can optionally come together to form a ring;
$R^3$ and $R^4$ can optionally come together to form a ring;
and a compound selected from the group consisting of a saturated or unsaturated alkyl halide, saturated or unsaturated alkyl-O-sulfonyl alkyl, a saturated or unsaturated alkyl-O-sulfonyl aryl, a saturated or unsaturated alkyl-O-acyl, and a saturated or unsaturated epoxide, all of which may optionally be substituted by one or more substituents selected from the group consisting of protected hydroxy, alkyl, alkenyl, acyl, nitro, protected amino, halo, protected carboxy, epoxide and cyano; and separating and isolating the compound of Formula IV.

* * * * *